US006290955B1

(12) United States Patent
Thierfelder

(10) Patent No.: US 6,290,955 B1
(45) Date of Patent: Sep. 18, 2001

(54) ANTIBODIES AGAINST T CELLS AS THERAPEUTICS

(75) Inventor: Stefan Thierfelder, Eichenau (DE)

(73) Assignee: GSF-Forschungszentrum fur Umwelt und ges, Oberschleibheim (DE)

( * ) Notice: Subject to any disclaimer, the term of this patent is extended or adjusted under 35 U.S.C. 154(b) by 0 days.

(21) Appl. No.: 09/134,575

(22) Filed: Aug. 14, 1998

Related U.S. Application Data

(62) Division of application No. 08/737,798, filed as application No. PCT/EP95/01898 on May 19, 1995, now Pat. No. 5,830,473.

(30) Foreign Application Priority Data

Jun. 18, 1994 (DE) .................................. 44 21 391

(51) Int. Cl.[7] .......................... A61K 39/395; C07K 16/28
(52) U.S. Cl. .................................. 424/130.1; 424/133.1; 424/154.1; 530/387.1; 530/387.3; 530/388.1; 530/388.75; 530/868
(58) Field of Search .............................. 424/130.1, 133.1, 424/154.1; 530/387.1, 387.3, 388.1, 388.75, 868

(56) References Cited

FOREIGN PATENT DOCUMENTS 0336379      4/1989   (EP) .

OTHER PUBLICATIONS

Lockwood, CM et al. Lancet 341:1620–22, Jun. 1993.*
Mathieson, PW et al. New Eng. J. Med. 323(4):250–254, Jul. 1990.*
Vandervegt et al, *J. Exp. Med.*, 177:1587–1592 (1993).
Kremmer et al, *Trans. Proc.*, 25(1):842–843 (1993).
Harlow et al, *In Antibodies: A Laboratory Manual*, Harlow and Lanes, eds., Cold Spring Harbor Laboratory, Cold Spring Harbor, NY, pp. 354–355 (1988).
International Search Report vol. 140/No. 11/Jun. 1, 1998, Baltimore U.S.
*Eur. J. Immunol.*, 23(5):1017–1022 (1993), Coden:EJIMAF; ISSN: 0014–2980.
*Eur. J. Immunol.*, 24(10):2323–2328 (1994), Coden:EJI-MAF; ISSN:0014–2980.
XIVTH International Congress of the Transplantation Society, Paris, France, Aug. 16–21, 1992.

* cited by examiner

*Primary Examiner*—Christina Y. Chan
*Assistant Examiner*—F. Pierre VanderVegt
(74) *Attorney, Agent, or Firm*—Sughrue, Mion, Zinn, Macpeak & Seas, PLLC

(57) ABSTRACT

A pharmaceutical kit and process useful for achieving prolonged immunosuppression and tumor cell elimination, wherein the kit comprises a first antibody having binding specificity for T cells and is capable of eliminating T cells in vivo; and a second antibody, having binding specificity for T cells and is capable of eliminating T cells in vivo, capable of modulating the antigen effect of T cells or both, wherein said first antibody differs from said second antibody in the constant region of its heavy chains and thus belongs to a different animal species, wherein said first antibody and said second antibody are maintained separately in said kit, and wherein in said process said first antibody is first applied once or several times and said second antibody is applied at a different time from said first antibody.

1 Claim, 3 Drawing Sheets

FIG. 3

| FIRST ANTIBODY | IMMUNIZATION | SECOND ANTIBODY | IMMUNIZATION | ANTI-ANTIBODIES* |
|---|---|---|---|---|
| RmT1 (RAT ANTI-MOUSE Thy-1) | -3 | RmT1 | 0, 14, 21 | 254 +/- 91.5 |
| MmT1 (MOUSE ANTI-MOUSE Thy-1.2) | -3 | RmT1 | 0, 14, 21 | 2.45** |
|  |  | RmCD4+CD8 | 0, 9, 19 | 84.2 +/- 154.2 |
| MmT1 | -3 | RmCD4+CD8 | 0, 9, 19 | 1.09 +/- 1.4 |
| RmCD4 (RAT ANTI-MOUSE CD4) | -3 | MmT1 | 0, 9 | 23.9 |
|  |  | MmT1 | 0, 9 | 0.25 +/- 0.43 |
| RmCD4 + CD8 (RAT ANTI-MOUSE CD4 + CD8) | -3 | MmT1 | 0, 9 | 0.79 +/- 1.07 |

*-μg/ml SERUM (MEAN VALUE+/- SD)
**- IN 3 OF 4 MICE NO ANTIBODIES COULD BE DETECTED AT ALL.

ANTIBODIES AGAINST T CELLS AS THERAPEUTICS

This is a Divisional of U.S. patent application No. 08/737,798, filed May 7, 1997, now U.S. Pat. No. 5,830,473; which is a National Stage Filing under 35 U.S.C. § 371 of PCT/EP95/01898, filed May 19, 1995.

FIELD OF THE INVENTION

The present invention relates to antibodies against T cells which are useful as therapeutic agents for prolonging immunosuppression and for tumor cell elimination.

BACKGROUND OF THE INVENTION

Heretofore, transplant rejection has been treated with immunosuppressant agents, e.g., monoclonal, immunosuppressive antibodies against human T lymphocytes which have been generated from mice, rats or golden hamsters. However, the effect of these antibodies is limited, since the patient develops an immunoreaction to antibodies which are derived from another animal species. This results in what are called antiantibodies, which inhibit the immunosuppressive effect of the injected monoclonal antibodies. Thus, at present, e.g., patients with kidney transplants that suffer from transplant rejection crises, are usually treated with only a single antibody therapy. If another rejection crisis occurs, this treatment is usually not repeated because of the possible formation of antiantibodies.

So far, there is no clinical therapy of choice for prolonging the immunosuppressive effect of antibodies while avoiding the formation of antiantibodies. A repeated treatment with another monoclonal antibody can lead to an accelerated formation of antiantibodies (Chatenoud, *Transpl. Proc.*, 25. 2(Suppl. 1):68 (1993)). In addition, patients have developed antiantibodies even against immunosuppressive antibodies that had been humanized using genetic engineering methods, i.e., where the antibodies have been substantially adapted to the patient's species, i.e., "primate species" or "species-adapted" antibodies (Isaacs et al, Lancet., 340:748 (1992)).

Experimentally, a clear prolongation of the survival time of skin transplants has been found in a mouse model, which was considered a tolerance induction. Such prolongation was observed after the injection of high doses of a rat antibody directed to mouse T(L3T4+Lyt–2) cells, followed by injection of a second antibody of the same species and the same cell binding specificity, which, however, differed from the first antibody by its low elimination of T cells from the blood circulation of the mouse (a "non-depleting", i.e., eliminating antibody). Unlike the present invention, the described principle of action therein was not based on a combined therapy of at least two antibodies with species-different Fc regions (Cobbold et al, *Eur. J. Immunol.*, 20:2747 (1990)).

Prolonged survival time of skin transplants and lack of formation of antiantibodies, were also found after the injection of a rat anti-mouse T(L3T4=CD4+lymphocyte subpopulation)-cell antibody, followed by injection of (Fab')₂ fragments and unfragmented monoclonal hamster anti-mouse T(CD3) antibodies (Hirsch et al, *Transplantation*, 47:853 (1989)). Here, too, the described principle of action is not based on a combined therapy of two antibodies having species-different Fc regions that are directed to all T cells, as in the present invention, but, rather, on the suppression of the CD4+T lymphocyte subpopulation (Hirsch et al, *J. Immunol.*, 140:3766 (1988)) achieved by means of the first antibody, which is, however, not sufficient.

Permanent tolerance of skin transplants can be achieved in irradiated mice after transplantation of bone marrow of the donor of the skin transplant, while protecting anti-T cell antibodies (Thierfelder et al, *Blood*, 68:818 (1986)). However, this technique involves risks.

So far, there is no therapy of choice for definitely preventing the formation of antiantibodies in a patient in the case of conventional poly- or monoclonal immunosuppressive antibodies. The first clinical experiences with antibodies that have recently been humanized by means of genetic engineering show that antiantibodies may be formed (Isaacs et al, supra) similarly to what was seen with murine immunosuppressive anti-mouse T cell antibodies (Kremmer et al, *Eur. J. Immunolp.*, 23:1017 (1993)).

Also, a combination of immunosuppressive antibody treatment with chemotherapy, e.g., cyclophosphamide or busulfan, involves the risk of side-effects, particularly on hematopoiesis, and, also, on the transplanted tissue, due to lack of cell specificity of the chemotherapeutic agents (Cobbold et al, supra; and Leong et al, *Eur. J. Immunol.*, 22:2825 (1992)).

SUMMARY OF THE INVENTION

An object of the present invention is to provide antibodies for clinical therapy for prolonging the immunosuppressive antibody effect, while avoiding the formation of antiantibodies.

The above-described object of the present invention has been met by the use of antibodies against T cells as a therapeutic for prolonged immunosuppression and tumor cell elimination, wherein the antibodies consist of at least two different groups A, B, which are administered at different times and in which at least one antibody type of group B differs from at least one antibody type of group A in the constant regions of their heavy chains, and wherein group A, which is first applied once or several times, has a T-cell eliminating effect, whereas the other group B (which is applied at a different time) has a T-cell eliminating and/or T-cell antigen modulating effect.

BRIEF DESCRIPTION OF THE DRAWINGS

FIG. 3 is a table showing suppression of antiantibodies by Fc-region-incompatible monoclonal antibody the rapy.

DETAILED DESCRIPTION OF THE INVENTION

Figure 1:
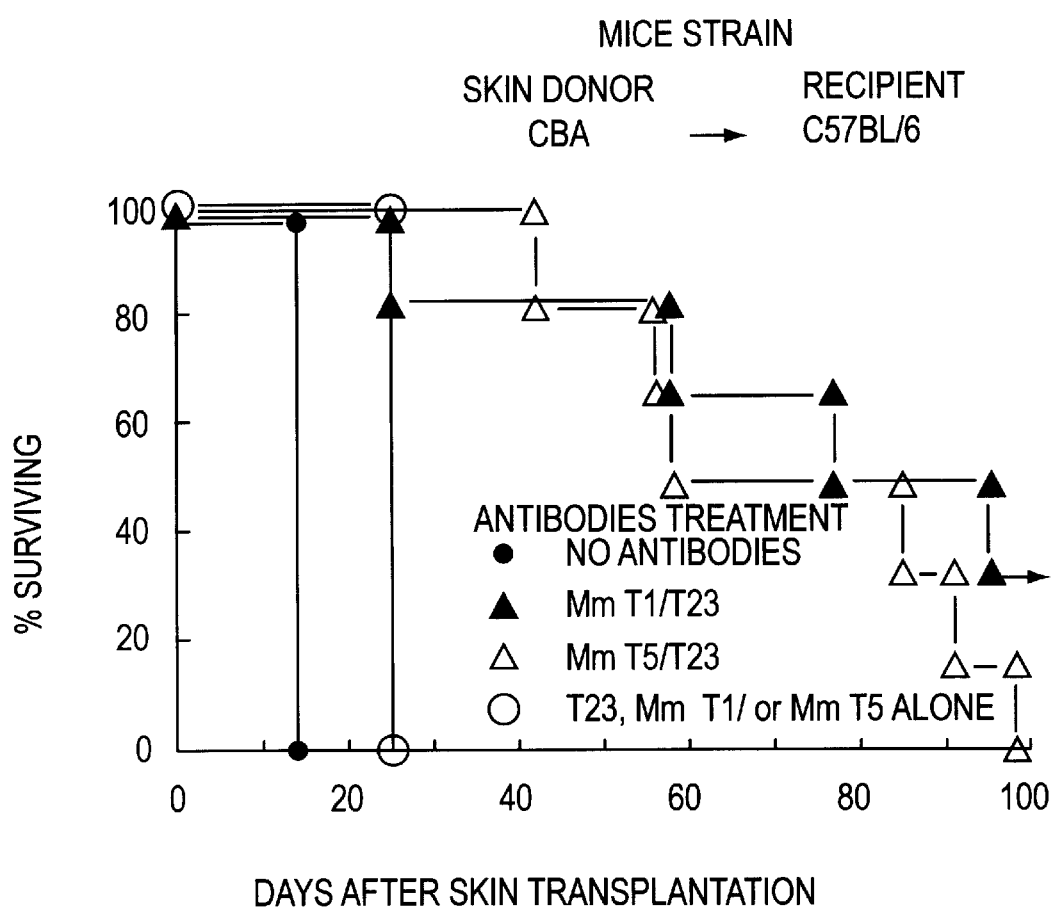
FIG. 1 is a graph showing prolonged immunosuppression due to sequential treatment with two anti-T cell antibodies, the Fc regions of which are species-different.

As discussed above, the above-described objects of the present invention have been met by the use of antibodies against T cells as a therapeutic for prolonged immunosuppression and tumor cell elimination, wherein the antibodies consist of at least two different groups A, B, which are administered at different times and in which at least one antibody type of group B differs from at least one antibody type of group A in the constant regions of their heavy chains, and wherein group A, which is first applied once or several ti mes, has a T-cell eliminating effect, whereas the other group B (which is applied at a different time) has a T-cell eliminating and/or T-cell antigen modulating effect.

Preferably, antibody B is a bispecific antibody.

Also, preferably, antibody B has a different constant region in its heavy chains than antibody A, and antibody A or antibody B is obtained by genetic engineering of the region encoding the constant region of its heavy chain.

Also, preferably, antibody A or antibody B is a humanized antibody.

Also, preferably, antibody A or antibody B has a hapten covalently linked to the constant region of its heavy chain. The hapten is preferably DNP or TNP.

Each of the two groups of antibodies, i.e., antibodies A and antibodies B, may also consist of only one antibody type or several kinds of antibodies.

In addition, the two groups of antibodies, i.e., antibodies A and antibodies B, may also be monoclonal or polyclonal.

The sequential treatment with anti-T cell antibodies that are partially or fully humanized using molecular biological means, and non-humanized antibodies, or with at least two anti-T cell antibodies generated from different species, as described herein, leads to prolonged immunosuppression and tumor cell elimination. This treatment principle has been experimentally tested on animals, as shown below, and has not heretofore been described in the art.

The novel therapy principle of the present invention, which has not heretofore been described in the art, is not obvious at all in terms of immunology. Commonly, immunobiologists and experts in the field of medicine, search for a reduction of the immunogenicity of anti-T cell antibodies (which causes the formation of antiantibodies) by adaptation thereof, as much as possible, to the patient's antibody immunoglobulin structures so that the patient is more likely to tolerate the antibodies, e.g., by humanization by means of genetic engineering of monoclonal immunosuppressive antibodies derived from mice. However, principally this adaptation cannot possibly be complete, and is the cause for the formation of antiantibodies, because the T cell binding (V) region of the immunosuppressive antibody is so variable that the patient's immunoapparatus can still form antiantibodies thereto.

The present invention is based on a contrasting experience, i.e., on the suppression of antiantibodies by creating a high species difference between the anti-T cell antibodies, wherein one or both, applied alone, may be potentially immunogenic in the recipient of the antibodies.

It was found in the present invention that:

(a) the survival time of skin transplants was basically prolonged, not by applying two different mouse anti-mouse T cell antibodies (or two different rat anti-mouse T cell antibodies) one after the other, but by using two antibodies which are species-different to one another, but not necessarily to the recipient of the antibodies, and a clear prolonged immunosuppression was achieved; and (b) two antibodies are effective even when they are as different from one another as human and mouse.

These thoughts, results and antibody combinations define a therapy model offering, inter alia, the advantage that it can immediately be tested clinically, and does not expose the patients to any additional treatment risks. A prolongation of immunosuppression should not only be a more successful therapy for rejection crises of organ transplants and immune complications with bone marrow transplantations, but should help prevent them altogether by prophylactic treatment. In addition, autoimmune diseases, chronic diseases of all kinds of rheumatism, and also individual tumor conditions might face new therapeutic perspectives. For instance, in the mouse model studies carried out by the inventors on the suppression of murine or human T cell leukemias transplanted into mice, a prolonged survival time due to antibody injection was observed. Upon T cell depletion, foreign immunocompetent cells can be introduced into chimeric mice, i.e., mice transplanted with bone marrow and suffering from leukemia, which foreign immunocompetent cells attack the neoplastic cells in the recipient. Furthermore, the tolerance induction, vis-à-vis heterologous serum proteins makes possible passive vaccination with antibodies of a different species that is free of hypersensitive reactions, e.g., for tetanus.

In the murine skin transplant model it could be shown that a monoclonal, immunosuppressive antibody, that was humanized by genetic engineering methods achieves a survival time of transplants against murine T lymphocytes, i.e., prolonged by a multitude, when its application was preceded by one or more injections of a monoclonal immunosuppressive mouse antibody. The preceding antibody injections as such did not have to be immunosuppressive in the sense of transplant prolongation. It turned out that this antibody therapy induced a complete tolerance towards heterologous, human serum protein, which still remained five months after the end of the immunosuppressive therapy. The unexpected prolongation of the immunosuppressive effect was thus, accompanied by a lack of a formation of antiantibodies in the treated mice due to their tolerance of the heterologous antibody immunoglobulin. The principle of action underlying this phenomenon is analyzed particularly with regard to species-related differences in the Fc region of the combined antibodies. It also proved effective when using anti-T cell antibodies that had not been modified by molecular biology, if they were species-different from one another.

Antibodies have what is called a variable region that includes the antibody binding site and what is called a constant Fc region that mediates antibody effector functions (e.g., elimination from the system of body cells occupied by antibodies), which is located on what are called the constant regions of the heavy chains of the antibody. In this way, two antibodies can be similar with regard to their specificity to bind, e.g., human T lymphocytes. Such antibodies with the same cell binding specificity, however, may differ in their Fc region due to the fact that they are derived from different normal or molecular biology-manipulated animal species. They can also be modified in vitro in the Fc region using methods of molecular biology on generating antibody-secretory cells (e.g., hybridomas or hybrid hybridomas) so that there is the degree of difference obtained as found between humans and rodents, and as described in the present invention.

In the following examples, the present invention is described in more detail.

EXAMPLE 1

Combination antibody treatment was carried out by first injecting a mouse $IgG_{2a}$ anti-mouse-Thy-1.2 antibody (MmT1 antibody; (Kremmer et al, supra)) on day 3, followed by injecting a chimeric antibody having a MmT1 idiotype (V region) and human Fc $IgG_1$ region (T23 antibody) on day 0 and twice a week. The T23 antibody differs from the MmT1 antibody by an exchange of the murine $IgG_1$ Fc region for a human $IgG_1$ Fc region, which was achieved by means of genetic engineering. The results are shown in FIG. 1.

As shown in FIG. 1, a single dose of MmT1 did not prolong the (average) skin survival time. T23 alone, applied twice a week, did prolong it by nine days from 16 to 24. MmT1 (first dose) followed by T23 (applied twice a week) prolonged it to more than 90 days. Thus, FIG. 1 shows immunosuppression that was prolonged approximately tenfold, as measured in a rodent skin transplantation model of maximum histoincompatibilty, by the combined Fc-region incompatible antibody treatment of the present invention.

Also, as shown in FIG. 1, a similarly increased immunosuppression was achieved after replacement of antibody MmT1 with antibody MmT5 (Kremmer et al, supra), which does not differ from antibody MmT1 in its T-cell specificity, but, rather, differs in the microstructure of the antibody binding site (idiotype).

The results demonstrate that in the combined Fc-region incompatible antibody therapy of the present invention, the likeness or difference of the antibody binding site is not a prerequisite for the principle of action, but, rather, the species-dependent difference of its heavy chains incorporating the Fc regions is a prerequisite for the principle of action.

EXAMPLE 2

MmT1 /RmCD4+CD8 combination therapy was carried out by injecting MmT1 on day 3, followed by injecting RmCD4+RmCD8 antibody (a rat anti-mouse CD4+CD8 lymphocyte antibody) on day 0 and twice a week, and vice versa. The results are shown in FIG. 2.

Figure 2:
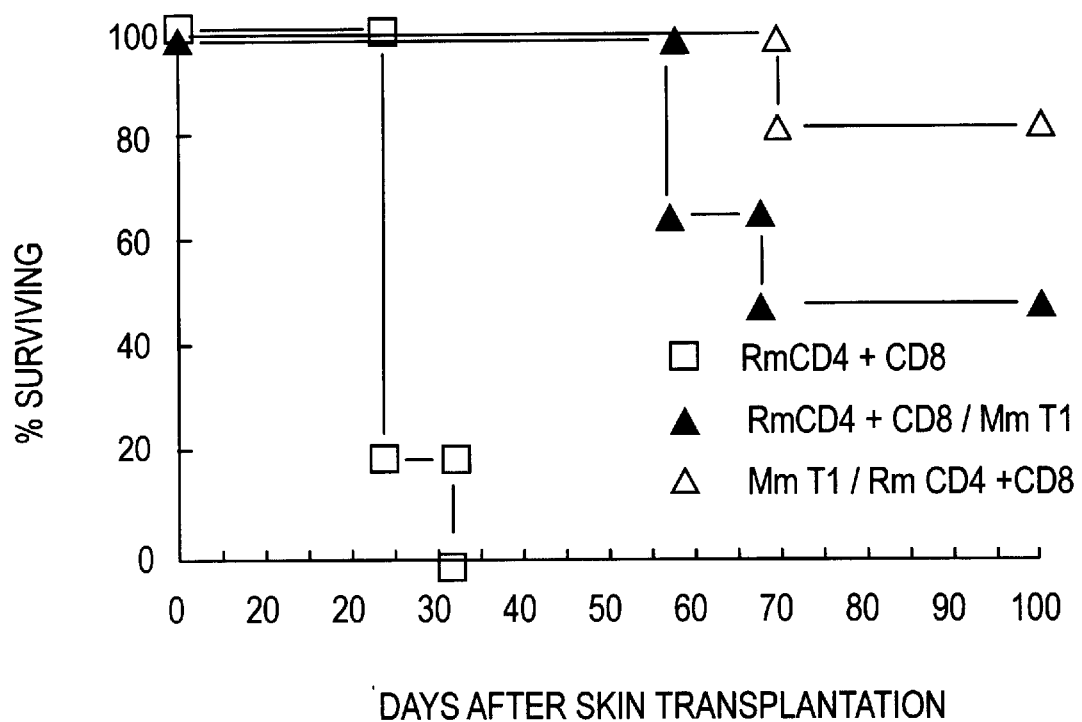
FIG. 2 is a graph showing immunosuppression using anti-T cell antibodies with mouse or rat Fc regions.

FIG. 2 shows that rat anti-mouse T cell antibodies having Thy-1 specificity (Kummer et al, *J. Immunol.*, 138:4069 (1987)), and also particularly clinically-relevant antibody specificities, such as anti-CD4 and anti-CD8 (two T cell subpopulations, which together bind all T cells) also prolong the average survival time of skin transplants. Furthermore, as shown therein, the reversal of the combined antibody treatment in the RmCD4+CD8/MmT1 combination also leads to a prolonged immunosuppression since here, too, the prerequisite of the species-dependent difference of the Fc region is fulfilled. Since anti-CD4+CD8 antibodies are active as first antibodies, this excludes an effect of the preinjected first antibody restricted to MmT1. On the contrary, the prerequisite for the synergistic antibody action of their species-dependent Fc region differences (apart from the application of at least two antibodies at different times) applies again and again. Survival of skin transplants using a combination antibody therapy was permanent if further T cell depleting and/or T cell receptor modulating (anti-CD3) antibodies were added to the second antibody.

EXAMPLE 3

Groups of 4 to 6 C57BL/6 mice were injected with 400 µg of the first antibody (shown in FIG. 3) and 500 µg of the second antibody (shown in FIG. 3). Tail blood was drawn 6 to 10 days after the last injection in order to determine the antiantibody level. The results are shown in FIG. 3.

As shown in FIG. 3, the combined rat/mouse or mouse/rat Fc-region incompatible antibody treatment leads to a high suppression or complete lack of the formation of antiantibodies, i.e., antiantibody levels were extremely low or zero where there was a species difference (rat/mouse or mouse/rat) between the first and the second antibody. The same applies to treatment when carried out as per Example 1.

Antiantibodies also occur when treating with polyclonal antibodies that arise after immunization of, e.g., rabbit, rat or horse lymphocytes. Here, too, it can be seen that a species difference (e.g., rabbit/rat) of polyclonal antibodies leads to a prolonged immunosuppression in mice, as well as with what are called bispecific antibodies, i.e., antibodies having two different binding sites, or with anti-T cell antibodies that were chemically modified by introduction of a low-molecular compound (e.g., DNP, TNP haptenes) or by genetic engineering, e.g., antibodies and antibody fragments prepared in bacteria. Here, too, sequentially injected anti-T cell antibodies may neutralize the formation of antiantibodies to species-different polyclonal or bispecific or chemically or molecular biology-modified antibodies. A prerequisite is always a strong difference in the sequentially applied antibodies or antibody groups, which either results from species difference or from the introduction (conjugation) of chemical compounds.

Finally, undesired immunoreactions may also occur in the case of passive immunization with antibodies in protein-oversensitive or presensitized patients. A treatment using combined Fc-region incompatible antibody therapy would prevent the formation of antiantibodies.

What is claimed is:

1. A method for prolonged immunosuppression comprising administering, to a subject in need of said immunosuppression, a pharmaceutically effective amount of a first antibody, having binding specificity for all of said subject's T cells and which is capable of depleting substantially all of said T cells in vivo, and thereafter administering a pharmaceutically effective amount of a second antibody having binding specificity for all of said subject's T cells and which is capable of prolonging said depletion of said T cells in vivo, or is capable of modulating the antigen effect of said T cells or is both capable of prolonging said depletion of said T cells in vivo and capable of modulating the antigen effect of said T cells, wherein said first antibody has a heavy chain constant region which is of a different animal species than the heavy chain constant region of said second antibody.

* * * * *